United States Patent [19]
Cho et al.

[11] Patent Number: 5,783,609
[45] Date of Patent: Jul. 21, 1998

[54] PROCESS FOR RECOVERING ORGANOALKOXYSILANE FROM POLYORGANOSILOXANE

[75] Inventors: Tsurahide Cho, Tokyo; Yoshiro Ohta, Kanagawa; Toshitsura Cho, Tokyo; Tohru Yamashita, Tokyo; Nobuaki Ohkawa, Tokyo; Makoto Nishida, Tokyo, all of Japan

[73] Assignees: Tama Chemicals Co., Ltd.; Toshiba Silicone Co., Ltd., both of Tokyo, Japan

[21] Appl. No.: 666,458

[22] PCT Filed: Dec. 28, 1994

[86] PCT No.: PCT/JP94/02281

§ 371 Date: Jun. 27, 1996

§ 102(e) Date: Jun. 27, 1996

[87] PCT Pub. No.: WO95/18174

PCT Pub. Date: Jul. 6, 1995

[30] Foreign Application Priority Data

Dec. 28, 1993 [JP] Japan ................... 5-334084

[51] Int. Cl.$^6$ ........................... C08G 77/01
[52] U.S. Cl. .................. 521/47.5; 528/20; 528/12
[58] Field of Search ............. 521/47.5; 528/12, 528/20

[56] References Cited

U.S. PATENT DOCUMENTS

| 2,392,713 | 1/1946 | Wright et al. ............. 521/47.5 |
| 3,099,671 | 7/1963 | George et al. ............. 521/47.5 |

FOREIGN PATENT DOCUMENTS

| 0527436 | 2/1993 | European Pat. Off. . |
| 0597294 | 5/1994 | European Pat. Off. . |
| 33-2149 | 3/1958 | Japan . |
| 59-179537 | 10/1984 | Japan . |
| 404835 | 10/1973 | U.S.S.R. ............. 521/47.5 |
| 1509364 | 9/1989 | U.S.S.R. ............. 521/47.5 |
| 94/16005 | 7/1994 | WIPO . |

OTHER PUBLICATIONS

Database WPI Derwent Publications Ltd., London, GB; AN AN83-704016 & SU 952 895 (Shalaev B. I.), Aug. 23, 1982 * abstract * & SU 952 895 A (Shalaev B.I.) Aug. 23, 1982.
Patent Abstracts of Japan vol. 013, No. 384 (C-629), Aug. 24, 1989 & JP 01 132590 A (Toshiba Silicone Co Ltd) May 25, 1989 * abstract *.

Primary Examiner—Ralph H. Dean
Attorney, Agent, or Firm—Jordan and Hamburg

[57] ABSTRACT

A process which comprises reacting a high molecular weight polyorganosiloxane or a composition containing the same with an alkoxysilane and/or a partially hydrolyzed condensate thereof at a temperature of lower than 300° C. in the presence of an alcoholate compound and recovering the resulting organoalkoxysilane and, in addition thereto, at least one of a distillable polyorganosiloxane low molecular weight compound, a non-volatile liquid polyorganosiloxane and a silica; and a process which comprises reacting a high molecular weight polyorganosiloxane or a composition containing the same with an alcoholate compound at a temperature of 50° to 150° C. in an anhydrous state and recovering the resulting distillable polyorganosiloxane low molecular weight compound and, in addition thereto, at least one of an organoalkoxysilane and a non-volatile liquid polyorganosiloxane.

33 Claims, No Drawings

PROCESS FOR RECOVERING ORGANOALKOXYSILANE FROM POLYORGANOSILOXANE

BACKGROUND OF THE INVENTION

This invention relates to a process for recovering a useful silicon-containing compound such as an organoalkoxysilane and/or a polyorganosiloxane low molecular weight compound, etc. by using a high molecular weight polyorganosiloxane or a composition containing the same as a starting material. In particular, it relates to a process for recovering an industrially useful silicon-containing compound from the above starting material which is a waste.

By significant spread of silicone rubbers, the amount of a silicone rubber waste which is vulcanized (hereinafter used as a general term of a crosslinking reaction for forming a rubbery elastic material) has been increased significantly. Also, when a silicone rubber is molded, for example, when flashes are removed, a residue of a vulcanized silicone rubber containing relatively less impurities other than a filler is generated. Silicone rubbers have been used frequently for making a model or for reproduction, and wastes thereof have been increased. Particularly, among silicone rubbers, in a moisture curing type liquid silicone rubber which has been used as a sealing material for construction, an adhesive or sealing material for industrial use, etc., there are materials which are cured after opening a package without use, or cured on a masking tape and discharged. On the other hand, there have been generated wastes of a silicone oil which is deteriorated by being used as a heating medium or an insulating oil, a used silicone grease for preventing salt damage and air pollution by dust, a semi-cured product or a cured product of a silicone resin for coating or for electric insulation, etc. in addition to silicone rubbers.

All of these contain a high molecular weight polyorganosiloxane, and the silicone rubbers and silicone grease further contain a filler such as a silica, etc. Heretofore, most of them have been disposed of as industrial wastes.

In U.K. Patent No. 716,024, there has been disclosed a process for regenerating a vulcanized silicone rubber waste by partially hydrolyzing a vulcanized silicone rubber using superheated steam. However, in this process, a filler existing in said silicone rubber cannot be separated so that the process has a utility value at most for reusing it as a silicone rubber by mixing it with an unvulcanized silicone rubber.

In U.S. Pat. No. 2,673,843, there has been disclosed a process for partially depolymerizing a silicone rubber by carrying out treatment with acid anhydride at about room temperature. By this process, a mixture of volatile polysiloxane low molecular weight compounds (oligomers) can be obtained. However, before reusing it, complicated steps for removing an acid and, depending on the case, a filler are required.

In West German Patent No. 875,046, there has been disclosed a process for preparing a cyclic polydialkylsiloxane by heating a hydrolyzed mixture comprising a dialkylsiloxane unit and a monoalkylsiloxane unit in the absence of oxygen. However, there have been not described utilization of a vulcanized silicone rubber nor separation of a filler from a product in that case.

Voronkov has reported that a methylalkoxysilane and a methylalkoxysiloxane are produced by adding an alcohol and a tetraalkoxysilane to a polydimethylsiloxane such as octamethylcyclotetrasiloxane and heating the mixture by using potassium hydroxide as a catalyst (J. Gen. Chem. Vol. 28, p. 2,128 (1958), etc.). However, it has been not described to obtain an organoalkoxysilane from a composition prepared by formulating a filler into a high molecular weight polyorganosiloxane and from a cured product thereof. Also, it has been not described to recover a cyclic polyorganosiloxane low molecular weight compound, in addition to the organoalkoxysilane.

In Japanese Provisional Patent Publication No. 132590/1989, it has been disclosed that by reacting a polyorganosiloxane with an alkoxysilane in the presence of a titanium compound such as tetrabutyl titanate, an organoalkoxysilane which is different from the alkoxysilane used can be obtained. Also here, the polyorganosiloxane used is a low molecular weight compound or a polyorganohydrogen siloxane, and there is an advantage that various organoalkoxysilanes such as one having a Si—H bond in a molecule, etc. can be obtained optionally. However, disclosed use of a high molecular weight polyorganosiloxane, on one containing a filler, or a cured product thereof, as in the present invention.

In Japanese Provisional Patent Publication No. 271416/1993, there has been disclosed a thermal decomposition process in which a volatile siloxane generated by heating a silicone rubber vulcanized product is condensed. In this process, it is required to carry out heating at a high temperature exceeding 350° C., and only a cyclic dialkylsiloxane is obtained.

When the foregoing is summarized, in the publications other than Japanese Provisional Patent Publication No. 271416/1993 described above in which thermal decomposition is carried out at high temperature, there is either no description about application to a silicone rubber vulcanized product, or complete depolymerization thereof cannot be effected, and/or separation of a filler is insufficient. Further, the resulting organic silicon compound is either an organoalkoxysilane or a volatile siloxane, and there has not been known a process by which both of them can be produced depending on conditions.

OBJECTS AND SUMMARY OF THE INVENTION

An object of the present invention is to solve the problems of the prior art as described above, and provide a process for recovering a useful compound from a high molecular weight polyorganosiloxane or a composition containing the same. The invention particularly seeks to recover a useful compound from industrial waste, and can be applied to any liquid or solid high molecular weight polyorganosiloxane type substance such as a high molecular weight polyorganosiloxane or a cured product thereof and a high molecular weight polyorganosiloxane composition containing a filler or a cured product thereof, etc. Additionally, the inventive process can regenerate a silicon compound such as an organoalkoxysilane and/or a volatile polyorganosiloxane low molecular weight compound, etc. at a relatively mild temperature of lower than 300° C. by selecting the processing conditions. Another object of the present invention is to provide a process for easily separating a filler contained in a high molecular weight polyorganosiloxane composition or a cured product thereof and regenerating and recovering the silicone compound when said composition or a cured product thereof is used as a starting material.

The present inventors have studied intensively in order to solve the above technical tasks and consequently found that by adding an alkoxysilane (particularly a tetraalkoxysilane) to a high molecular weight polyorganosiloxane such as a silicone rubber cured product or a composition containing the same and subjecting the mixture and a specific range of an alcoholate compound to heating treatment, said polyorganosiloxane can be easily slurried and decomposed to be converted into a useful silicon-containing compound such as an organoalkoxysilane having the number of hydrocarbon groups directly bonded to silicon atoms, which is larger than that of the alkoxysilane used in the reaction, and further found that even when the above alkoxysilane is not used, a high molecular weight polyorganosiloxane can be decomposed in the same manner merely by the above alcoholate under specific conditions to be converted into a useful silicon-containing compound such as a polyorganosiloxane low molecular weight compound, to accomplish the present invention.

DETAILED DESCRIPTION OF THE INVENTION

The first process for recovering a silicon-containing compound from a high molecular weight polyorganosiloxane of the present invention comprises:

(I) reacting (A) a high molecular weight polyorganosiloxane or a composition containing the same, (B) in the presence of at least one alcoholate compound selected from an alkali metal alcoholate and a quaternary ammonium alcoholate, with (C) an alkoxysilane represented by the formula: $R^1{}_m Si(OR^2)_{4-m}$ (wherein $R^1$ represents a substituted or unsubstituted monovalent hydrocarbon group having 1 to 6 carbon atoms; $R^2$ represents an alkyl group with a carbon number of 1 to 6; and m is 0, 1 or 2); and/or a partially hydrolyzed condensate thereof in such an amount that the total number of alkoxy groups existing in the above (B) and (C) is 0.1 or more based on one silicon atom existing in the high molecular weight polyorganosiloxane in (A), or in such an amount that the above total number of alkoxy groups is 0.1 or more and less than 1 when (A) is a liquid or semi-solid chain-structure polydiorganosiloxane, at a temperature of lower than 300° C.; and (II) recovering the resulting (a) an organoalkoxysilane represented by the formula: $R^4{}_n Si(OR^5)_{4-n}$ (wherein $R^4$ represents a substituted or unsubstituted monovalent hydrocarbon group derived from $R^1$ and the polyorganosiloxane; $R^5$ represents an alkyl group with a carbon number of 1 to 6; and n is 1, 2 or 3 and also an integer satisfying n>m); or at least one of the following (b) to (d) in addition to (a)

(b) a distillable polyorganosiloxane low molecular weight compound having 2 to 8 silicon atoms in the molecule;

(c) a non-volatile liquid polyorganosiloxane having a weight average molecular weight of less than 1,000; and (d) a silica.

Further, the second process comprises:

(I') reacting (A) a high molecular weight polyorganosiloxane or a composition containing the same with (B) at least one alcoholate compound selected from an alkali metal alcoholate and a quaternary ammonium alcoholate, under conditions of a reaction temperature of 50° to 150° C. and a water content in the reaction system of 3,000 ppm or less; and (II') recovering the resulting (b) a distillable polyorganosiloxane low molecular weight compound having 2 to 8 silicon atoms in a molecule; or in addition to (b)

(a) an organoalkoxysilane represented by the formula: $R^4{}_n Si(OR^5)_{4-n}$ (wherein $R^4$ represents a substituted or unsubstituted monovalent hydrocarbon group derived from $R^1$ and the polyorganosiloxane; $R^5$ represents an alkyl group with a carbon number of 1 to 6; and n is 1, 2 or 3 and also an integer satisfying n>m); and (c) a non-volatile liquid polyorganosiloxane having a weight average molecular weight of less than 1,000.

The first process of the present invention includes (I) a decomposition reaction of the high molecular weight polyorganosiloxane in Component (A) in the presence of (B) the alcoholate compound and (C) the alkoxysilane and (II) recovery of (a) the organoalkoxysilane obtained by the reaction or various kinds of silicon-containing compounds in addition thereto. Further, the second process includes (I') a decomposition reaction of Component (A) in the presence of the above Component (B) and (II') recovery of (b) the polyorganosiloxane low molecular weight compound obtained by the reaction or various kinds of silicon-containing compounds in addition thereto. (I) or (I') and (II) or (II') may be carried out successively or may be carried out simultaneously. Between (I) or (I') and (II) or (II'), there may be inserted a step of removing solids existing in Component (A) or formed by (I) or (I'), by solid-liquid separation such as filtration, etc. However, one of the characteristics of the present invention is that (I) or (I') and (II) or (II') can be carried out successively or simultaneously without adding such a removing step.

Component (A) to be used as a starting material of Reaction (I) or (I') in the present invention is a high molecular weight polyorganosiloxane or a composition containing the same. Here, the high molecular weight polyorganosiloxane is a polyorganosiloxane substantially having no volatility and representatively having an average molecular weight of 1,000, to 800,000 or a compound having a larger network molecular structure, formed by a vulcanization (crosslinking) reaction thereof. A small amount of a polyorganosiloxane having a lower molecular weight may be mixed because of the reasons that these are used without purification or decomposed during use, or added intentionally depending of the purpose of use, etc. The skeleton based on a siloxane bond thereof may be either straight, branched or network. As a representative, there may be mentioned a straight polydiorganosiloxane as seen in a base polymer of a silicone rubber or a silicone oil, or a network polymer in which they are crosslinked by a siloxane bond, to which the process of the present invention can be applied advantageously. Further, depending on a crosslinking mechanism, there may exist a small amount of silethylene crosslinking or other crosslinking structure including a carbon chain in a molecule. As a representative example of the high molecular weight polyorganosiloxane containing no filler, obtained by crosslinking a chain-structure polydiorganosiloxane, there may be mentioned a silicone gel. In the following, such a straight polydiorganosiloxane and a crosslinked polyorganosiloxane derived therefrom are generally called a chain-structure type polyorganosiloxane.

Another representative example is a polyorganosiloxane having a highly networked molecular skeleton, which is called a silicone resin.

In the high molecular weight polyorganosiloxane existing in Component (A), organic groups bonded to silicon atoms are not particularly limited, but may be exemplified by, other than the above crosslinking group existing in a small amount, an alkyl group such as methyl, ethyl, propyl, butyl, pentyl, hexyl, decyl, etc.; an aryl group such as phenyl, etc.; an aralkyl group such as 2-phenylethyl and 2-phenylpropyl; and a monovalent substituted hydrocarbon group such as 3,3,3-trifluoropropyl, etc. In addition thereto, a small amount(s) of an alkenyl group such as vinyl (uncrosslinked), etc.; and/or a monovalent substituted hydrocarbon group such as 3-aminopropyl, N-(2-amino-ethyl)-3-aminopropyl, 3-glycidoxypropyl, etc. may exist in a molecule. In the case of common silicone oils and silicone rubbers, all or most of the organic groups are methyl groups. In order to carry out the reaction and recovery advantageously, those mainly having methyl groups are preferred, and those having organic groups substantially all of which except for the above crosslinking group are methyl groups are particularly preferred. Among silicone oils and silicone resins, there is a type having methyl groups and phenyl groups, and the process of the present invention can also be applied to such a type advantageously.

Further, the great characteristic of the present invention is that the process of the present invention can be also applied advantageously to a composition obtained by formulating a filler and/or a pigment and other additive into the above high molecular weight chain-structure type polyorganosiloxane, such as an uncured silicone rubber, a silicone grease, etc. and a product obtained by crosslinking it, such as a cured silicone rubber. As the filler and/or the pigment, there may be mentioned a silica such as aerosol silica, precipitated silica, silica aerogel, pulverized silica, fused silica and diatomaceous earth; and titanium oxide, aluminum oxide, zinc oxide, iron oxide, zeolite, clay, glass, gypsum, barium sulfate, zirconium silicate, calcium carbonate, carbon black, graphite, etc. These fillers and/or pigments may be used singly or may be used as a mixture of two or more kinds. Further, these fillers may be used as such, or the surfaces of them may be treated with an organic silicon compound such as a straight polydimethylsiloxane, octamethylcyclotetrasiloxane, trimethylchlorosilane, dimethyldichlorosilane and hexamethyldisilazane.

The content of solid components other than the polyorganosiloxane, such as the filler and the pigment is not particularly limited, but it is preferably 40% by weight or less, more preferably 20% by weight or less in the composition to be used as Component (A) in order to make the reaction and a separation treatment subsequent thereto proceed smoothly.

Further, the present invention can also be applied to a high molecular weight polyorganosiloxane or a composition containing the same and the filler, in each of which an organic solvent is contained.

As Component (A) as described above, there may be used wastes generated in various industrial fields, i.e., a waste which is a waste silicone oil, a waste silicone grease, a waste silicone gel, an uncured or cured silicone rubber (including a silicone sealing material and a silicone rubber sponge) or a semi-cured or cured silicone resin.

In Reaction (I), Component (B) to be used in the present invention itself decomposes Component (A) and also functions as a catalyst for reacting Component (A) with Component (C). Further, in Reaction (I'), it acts as a decomposing agent of Component (A). The alcoholate compound to be used as Component (B) may be exemplified by an alkali metal alcoholate such as lithium methylate, sodium methylate, potassium methylate, lithium ethylate, sodium ethylate, potassium ethylate, sodium isopropylate, etc.; and a quaternary ammonium alcoholate such as tetramethylammonium methylate, tetraethylammonium methylate, tetramethylammonium ethylate, etc. They may be used singly or in combination of two or more kinds, and, for a catalytic effect, sodium methylate is preferred. For example, when Component (B) is an alkali metal alcoholate, it can be obtained as an alcohol solution of alcoholate by reacting a corresponding alkali metal with an excess alcohol. In the present invention, it may be used in the form of such an alcohol solution.

The amount of Component (B) to be used is not particularly limited, but it is generally 0.1 to 100 parts by weight, preferably 0.5 to 50 parts by weight, more preferably 3 to 15 parts by weight based on 100 parts by weight of the high molecular weight polyorganosiloxane contained in Component (A). If the amount of Component (B) to be used is less than 0.1 part by weight, the decomposition reaction of the high molecular weight polyorganosiloxane does not proceed well. On the other hand, if it is used in an amount exceeding 100 parts by weight, a more catalytic effect cannot be obtained, which is economically disadvantageous.

Component (C) to be used in Reaction (I) of the present invention not only acts as a decomposing agent of the polyorganosiloxane in Component (A), but also contributes as a refluxing agent for making the reaction proceed under stable conditions. Component (C) is an alkoxysilane and/or a partially hydrolyzed condensate thereof, which becomes an alkoxy group source for producing the organoalkoxysilane (a) having a number of organic groups bonded to silicon atoms, which is larger than that of Component (C), by decomposing Component (A).

The alkoxysilane is represented by the formula: $R^1_m Si(OR^2)_{4-m}$ (wherein $R^1$, $R^2$ and m are as described above). As $R^1$, there may be mentioned a straight or branched alkyl group such as methyl, ethyl, propyl, butyl, pentyl and hexyl; a cycloalkyl group; a phenyl group; and a substituted hydrocarbon group such as a chloromethyl group. Based on reactivity, methyl and ethyl are preferred, and since (a) having methyl groups which can be recovered easily can be obtained, a methyl group is particularly preferred. As $R^2$, there may be mentioned methyl, ethyl, propyl, butyl, pentyl and hexyl, and it may be straight or branched. Based on reactivity, methyl and ethyl are preferred, and a methyl group is most preferred. Further, m is 0, 1 or 2, and, for availability, a tetraalkoxysilane in which m is 0 is most preferred, but a methyltrialkoxysilane in which $R^1$ is a methyl group and m is 1 is also preferred since it is derived from methyltrichlorosilane which is an excess component among methylchlorosilanes synthesized from methyl chloride and metallic silicon and also because recovery of a reaction product is easy as described above.

Also, as Component (C), there may be used a partially hydrolyzed condensate of such an alkoxysilane, which is advantageous for obtaining (a) efficiently by setting a high reaction temperature by raising the boiling point of Component (C) to be used and removing the organoalkoxysilane of (a) by evaporation to the outside of the reaction system during the reaction. For example, in the case of tetramethoxysilane or tetraethoxysilane, dimers, trimers or tetramers thereof or mixtures thereof may be used.

The amount of Component (C) to be used in Reaction (I) is such an amount that the total number of alkoxy groups in Component (B) and Component (C) is 0.1 or more based on one silicon atom existing in the high molecular weight polyorganosiloxane in Component (A), and when Component (A) exhibits a solid state, it is such an amount that said number is preferably 1 to 8, more preferably 2 to 4. If this stoichiometric ratio is less than 0.1, the decomposition reaction of the polyorganosiloxane in (A) does not proceed sufficiently. When Component (A) is a composition containing a large amount of the filler, it is advantageous to use Component (C) in an excess amount in order to make the reaction proceed smoothly and carry out removal of the filler by filtration easily after recovering (a) formed by the reaction by distillation.

On the other hand, when Component (A) is a liquid or in a semi-solid-state and is substantially a straight polydiorganosiloxane such as silicone oil and a silicone raw rubber, the reaction can proceed by using Components (B) and (C) in such amounts that the total number of alkoxy groups existing in the above Component (B) and Component (C) is 0.1 or more and less than 1 based on one silicon atom in said polydiorganosiloxane. By using such specific amounts of Components (B) and (C), as reaction products, there can be obtained not only (a) the organoalkoxysilane but also (b) the polyorganosiloxane low molecular weight compound and (c) the non-volatile liquid polyorganosiloxane at an optional ratio. Further, even when the filler exists in Component (A), the decomposition reaction can proceed. In order to obtain such (b) and/or (c), it is preferred to use a composition containing the chain-structure type polyorganosiloxane as Component (A).

In Reaction (I) or (I') of the present invention, in order to make the reaction proceed smoothly by dissolving Component (B) and helping other components to come into contact with Component (A) and facilitate reflux in Step (II) or (II') described below, (D) an alcohol may be used in addition to the essential components in the respective reactions. (D) is represented by the formula: $R^3OH$ (wherein $R^3$ is as described above), and an alcohol to be used as a reactant or a solvent when Component (B) is synthesized may be used as such, but it is preferred to further add an alcohol in order to make Reaction (I) or (I') proceed by reflux under relatively mild conditions. The alcohol to be further added may be one having an alkyl group which is the same as the alkyl group of the alcoholate compound of Component (B), but it may be selected optionally depending on a boiling point so that an optional reaction temperature can be obtained by reflux. In order to simplify the composition of the reaction product and facilitate purification by separation, it is preferred that the alkyl group of the alcoholate compound and $R^3$ are the same. As an example of the alcohol to be used, there may be mentioned methanol, ethanol, isopropanol and butanol. As an alkoxy-ended polydimethylsiloxane low molecular weight compound in (a) and (b), a methoxy type compound can be obtained so that it is preferred that Component (B) is an alkali metal methylate, when Component (C) is used, it is a methoxy type silane, and Component (D) is methanol.

With respect to the amount of Component (D) to be used, the total amount of Components (C) and (D) is preferably 50 to 1,000 parts by weight, more preferably 70 to 300 parts by weight based on 100 parts by weight of the polyorganosiloxane contained in Component (A). Particularly when Component (A) is a solid composition such a cured silicone rubber, it is effective to add such Component (D).

Further, particularly when a polyorganosiloxane having a highly networked molecular skeleton such as a silicone resin or a composition containing the same is used as Component (A), or even when the chain-structure type polyorganosiloxane is used as Component (A), an optional organic solvent may be used in combination in order to increase the solubility of the polyorganosiloxane to the system. The organic solvent to be used may be exemplified by a hydrocarbon solvent such as toluene, xylene, petroleum type hydrocarbon, etc.

The reaction of (I) in the present invention is carried out by reacting (A) the high molecular weight polyorganosiloxane or a composition containing the same with (C) the alkoxysilane in the presence of (B) the alcoholate compound. During the reaction, in order to make the reaction proceed smoothly, (D) the alcohol represented by the formula: $R^3OH$ (wherein $R^3$ is as described above) may be present.

The reaction proceeds under a condition of lower than 300° C. under which cleavage of the polyorganosiloxane is not effected under ordinary conditions. The reaction can proceed under mild conditions of vessel temperature being maintained at 250° C. or lower, more preferably at 70° to 160° C. by maintaining reflux temperature at 64° to 170° C., more preferably at 64° to 125° C. by refluxing excess Components (C) and (D). The reaction proceeds under normal pressure, but the reaction may be carried out under reduced pressure or pressurization. Particularly when recovery of a product is carried out simultaneously with the reaction, the reaction may proceed under reduced pressure depending on the boiling point of a product to be recovered. Further, depending on Component (D) to be used, in order to maintain the reaction temperature, the reaction may be carried out under pressurization.

Further, particularly when Component (A) is a cured composition containing a filler, it is preferred to maintain the water content in the reaction system at 3,000 ppm or less in order to facilitate formation of a slurry by the action of Component (B).

By the reaction, the siloxane bond contained in Component (A) is cleaved and alkoxy groups in Component (C) are bonded, whereby (a) the organoalkoxysilane is produced. Further, by using the total number of alkoxy groups in Components (B) and (C) in an amount of less than 1 based on one silicon atom in Component (A), (b) the polyorganosiloxane low molecular weight compound is produced in addition to (a) the organoalkoxysilane. Further, depending on the reaction conditions, (c) the non-volatile liquid polyorganosiloxane is also produced.

In order to make the reaction proceed smoothly and to obtain (a) with good efficiency, the reaction may proceed while (a) is removed by evaporation from the system by carrying out distillation at the boiling point of (a) to be produced or an optional temperature which is a temperature not lower than the azeotropic point of said (a) and Component (D) to be used and is lower than the boiling point of Component (C) to be used.

When Component (A) is a composition containing a filler and/or a pigment, said filler and/or pigment is/are dispersed in the reaction system as the reaction proceeds. Further, Component (C) is disproportioned to form (d) the silica. The filler in Components (A) and (d) produced as described above form a solid phase in the reaction system so that the system becomes a slurry and the reaction proceeds.

The reaction of (I') in the present invention is carried out by reacting (A) the high molecular weight polyorganosiloxane or a composition containing the same with (B) the alcoholate compound. During the reaction, in order to make the reaction proceed smoothly, (D) the alcohol represented by the formula: $R^3OH$ (wherein $R^3$ is as described above) may be present in the same manner as in Reaction (I). (A), (B) and (D) to be used here are the same as in Reaction (I). As Component (A), a composition containing the chain-structure type polyorganosiloxane is preferred.

In Reaction (I'), it is carried out at a reaction temperature of 50° to 150° C., preferably 64° to 125° C. without using Component (C). Further, in order to prevent hydrolysis of Component (B) or a produced alkoxy group-containing compound and also to help decomposition of Component (A) by Component (B), the reaction is made to proceed while maintaining the water content in the reaction system at 3,000 ppm or less, preferably 1,000 ppm or less. With respect to the reaction pressure, the reaction proceeds even under normal pressure, but it may be carried out under reduced pressure or pressurization. It is preferred to carry out the reaction under pressurization of 1 to 4 atmospheric pressure (gauge pressure).

In Reaction (I'), the high molecular weight polyorganosiloxane in Component (A) is decomposed to obtain (b) the distillable polyorganosiloxane low molecular weight compound and as by produce: (a) the organoalkoxysilane and (c) the non-volatile liquid polyorganosiloxane.

Also in Reaction (I'), in the same manner as in Reaction (I), when Component (A) is a composition containing a filler and/or a pigment, they are dispersed in the reaction system, the system becomes a slurry, and the reaction proceeds. However, when Component (A) is a cured composition containing a filler, if the water content in the reaction system exceeds 3,000 ppm, slurrying does not proceed sufficiently.

The compound (b) obtained in Reaction (I') is mainly a cyclic polydiorganosiloxane having 2 to 8 silicon atoms, and poly(di-organosiloxane) having an alkoxy at both ends is also partially produced.

The organoalkoxysilane of (a) which is obtained by Reaction (I) and also by-produced by Reaction (I') is represented by the formula: $R^4{}_nSi(OR^5)_{4-n}$ (wherein $R^4$, $R^5$ and n are as described above), and the alkoxy group $OR^5$ contained in (a) is derived from the alkoxy group $OR^2$ contained in Component (C) used in the reaction. Therefore, $R^5$ may be exemplified by the same groups of $R^2$.

$R^4$ is derived from both the organic groups bonded to silicon atoms of the high molecular weight polyorganosiloxane in Component (A) used as a starting material and $R^1$ of Component (C). One preferred embodiment of the present invention is that all of the organic groups bonded to silicon atoms of the high molecular weight polyorganosiloxane in Component (A) are methyl groups, or when Component (A) is a crosslinked chain-structure type polyorganosiloxane or a composition containing the same, substantially all of the above organic groups except for groups forming crosslinking are methyl groups, and $R^1$ of Component (C) is also a methyl group. In that case, $R^4$ of (a) recovered is a methyl group.

The compound (a) to be synthesized in the present invention is an organoalkoxysilane having a larger number of the organic groups bonded to silicon atoms than that of Component (C) to be used in the reaction. That is, when the compound in which m=0 is used as Component (C), n of (a) is 1, 2 or 3. Similarly, from a component (C) in which m=1, a compound (a) in which n is 2 or 3 is obtained, and from one in which m=2, one in which n is 3 is obtained. Depending on (C) used and the reaction conditions, different kinds of (a) are produced. However, as a preferred embodiment of the present invention, by using the chain-structure type polyorganosiloxane as Component (A) and using (C) in which m=0, i.e., a tetraalkoxysilane, a diorganodialkoxysilane in which n=2 can be obtained as (a) with excellent selectivity. As a representative example of such a diorganodialkoxysilane, there may be mentioned dimethyldimethoxysilane, dimethyldiethoxysilane, dimethyldiisopropoxysilane, methylphenyldimethoxysilane, methylphenyldiethoxysilane, diphenyldimethoxysilane and diphenyldiethoxysilane.

Compound (b) which is obtained by Reaction (I') and also produced in Reaction (I) depending on the formulation ratio of the starting materials used as described above is a polyorganosiloxane low molecular weight compound having 2 to 8 silicon atoms in the molecule. When the number of silicon atoms exceeds 8, it is difficult to reuse it by isolation due to distillation even when reduced pressure is used. When component (A) is the chain-structure type polyorganosiloxane or a composition containing the same, the polyorganosiloxane low molecular weight compound (b) recovered is a cyclic polydiorganosiloxane comprising a bifunctional siloxane unit and/or a both-ends dialkoxy poly(diorganosiloxane). As a preferred embodiment of the present invention, when Component (A) is the chain-structure type polyorganosiloxane having organic groups bonded to silicon atoms of 90 mole % or more, more preferably substantially all of which except for groups forming crosslinking are methyl groups, or a composition containing the same, and an alkoxysilane in which m=0, or m=1 and $R^1$ is a methyl group is used as Component (C), the resulting (b) is exemplified by hexamethylcyclotrisiloxane, octamethylcyclotetrasiloxane, decamethylcyclopentasiloxane, dodecamethylcyclohexasiloxane, etc. as the cyclic polydiorganosiloxane; and exemplified by 1,3-dialkoxy-1,1,3,3-tetramethyldisiloxane, 1,5-dialkoxy-1,1,3,3,5,5-hexamethyltrisiloxane, 1,7-dialkoxy-1,1,3,3,5,5,7,7-octamethyltetrasiloxane, etc. which have alkoxy groups corresponding to the kind of $OR^2$ of Component (C) to be used, as the both-ends dialkoxy poly(diorganosiloxane).

Compound (c) which is formed by Reactions (I) and (I') is a non-volatile liquid polyorganosiloxane in which a cleaving degree of the siloxane bond in the high molecular weight polyorganosiloxane in Component (A) is low and many siloxane chains are linked and remain, and its average molecular weight is less than 1,000. Most of or substantially all of the organic groups bonded to silicon atoms thereof are derived from said high molecular weight polyorganosiloxane, but organic groups derived from Component (C) may be partially present. As such a liquid polyorganosiloxane, there may be obtained one which is straight or branched depending on the molecular skeleton of said high molecular weight polyorganosiloxane, and the $OR^2$ group derived from Component (C) is present at a molecular end. However, when the molecular end of the high molecular weight polyorganosiloxane in Component (A) is terminated by a triorganosilyl group such as a trimethylsilyl group, said triorganosilyl group may be present at a partial molecular end of (c).

Step (II) or (II') in the present invention is a step of recovering the product of Reaction (I) or (I') by using an optional method such as distillation and others. As described above, (II) may be carried out successively after (I) or may be carried out simultaneously with (I) by using, for example, a reactor equipped with a distillation column. A preferred embodiment is that in the first stage, the reaction of (I) is carried out while carrying out reflux, and after an optional time, for example, 1 to 10 hours, is lapsed, unreacted substances and the reaction products (a) and (b) may be distilled out successively from the top of the column depending on the boiling points. Another embodiment is that recovery of the products from the reaction system is carried out once by simple distillation, and then the products are applied to rectification. Distillation may be carried out under normal pressure or reduced pressure depending on the boiling points. The same applies to Reaction (II) and Recovery (II').

In the present invention, unreacted Components (C) may remain in the distillate after the reaction. At the time of recovery, they are separated easily from the product due to the differences in their boiling points and can be reused for the reaction of the present invention.

In the production system obtained by Reaction (I) or (I'), the high molecular weight polyorganosiloxane may remain in Component (A) or (c) the non-volatile liquid polyorganosiloxane the molecular weight of which cannot completely be decreased, and an organic silicon compound which is a decomposition product derived from a crosslinking group portion. They remain as a distillation residue when recovering (a) and/or (b) which is/are the product(s). Further, when a composition containing a filler and/or a pigment is used as Component (A), a solid component thereof and a silica by-product of the reaction exist as a solid phase in the system.

In steps (II) and (II'), first (a) and/or (b) is/are removed by distillation from the production system. In this case, (a) which is the primary desired product in the production system in the case of Reaction (I) and only (b) in the case of Reaction (I') in the same manner can be purified and recovered, or all of the components which can be distilled may be recovered. Then, if necessary, the liquid phase and the solid phase may be separated from each other by a method such as centrifugation, filtration or decantation. From the liquid phase, the non-volatile liquid polysiloxane (c) can be recovered.

Further, in the solid phase, (d) the silica produced and a filler and/or pigment existing in the starting material Component (A) are contained. Both may be recovered as a mixture. Further, when decomposition of the high molecular weight polysiloxane is carried out in conditions under which (d) is not produced, the above filler and/or pigment can be recovered as such from the solid phase. When Component (A) which does not contain the filler and/or the pigment is used, (d) can be recovered easily as a solid phase which is obtained by the above solid-liquid separation.

Alternatively, as a first stage of the recovery step (II) or (II'), the reaction products of (I) or (I') may be subjected to solid-liquid separation by a method such as centrifugation, etc. Further, distillation may be carried out while Component (B) used in the reaction exists, but distillation of the volatile component may be carried out after deactivating Component (B) by neutralization by sending carbon dioxide or the like, and/or moving it into the solid phase completely by the above solid-liquid separation.

When (b) is removed by evaporation in the presence of (B), a part or whole of the straight polydiorganosiloxane having both ends each terminated by an alkoxy group in (b) are cyclized to generate a cyclic polydiorganosiloxane and a diorganodialkoxysilane which is (a). On the other hand, when removal of the volatile component by evaporation is carried out after deactivating or removing (B), the produced both-ends alkoxy chain-structure polydiorganosiloxane can be obtained as such. Thus, the purification step can be selected depending on the desired product.

Alternatively, Reaction (I) can be made further proceed by carrying out removal of the volatile component by evaporation in the presence of Component (B) at the boiling point of (a) or a temperature which is not lower than the azeotropic temperature of (a) and existing (D) and is lower than the boiling point of (C).

BEST MODE FOR PRACTICING THE INVENTION

In the following, the present invention is described in more detail by Examples and Comparative examples. In Examples and Comparative examples, parts always represent parts by weight. The present invention is not limited by these Examples.

In the following Examples, as Component (A), there were used Liquid high molecular weight polydiorganosiloxanes A-1 and A-3; Crosslinked high molecular weight polyorganosiloxane A-7; Composition A-6 containing a high molecular weight polydiorganosiloxane; and Cured compositions A-2, A-4 and A-5.

A-1: polydimethylsiloxane having a viscosity at 25° C. of 100 cSt and having both ends each terminated by a trimethylsilyl group;

A-2: a cured product having a siloxane content of 82% obtained by curing a high molecular weight polyorganosiloxane-containing composition containing polydimethylsiloxane having a viscosity at 25° C. of 20,000 cSt and having both ends each terminated by a silanol group, methyltris(methyl ethyl ketoxime)silane, aerosol silica and dibutyltin dilaurate, by contact with water in the air;

A-3: straight polymethylphenylsiloxane having a viscosity at 25° C. of 450 cSt, comprising 67 mole % of a dimethylsiloxy unit and 33 mole % of a diphenylsiloxy unit and having both ends each terminated by a trimethylsilyl group;

A-4: a cured product having a siloxane content of 67% obtained by curing a composition containing straight polydimethylvinylsiloxane having a viscosity at 25° C. of 20,000 cSt and having both ends each terminated by a dimethylvinylsilyl group; branched polymethylvinylsiloxane comprising a dimethylvinylsiloxy group, a trimethylsiloxy group and a $SiO_2$ unit; polymethylhydrogen siloxane comprising a methylhydrogen siloxy unit, having both ends each terminated by a trimethylsilyl group and having a viscosity at 25° C. of 40 cSt; fused silica and a catalytic amount of a platinum compound, by heating at 130° C.;

A-5: a cured product having a siloxane content of 71% obtained by mixing 2,5-dimethyl-2,5-di(tert-butylperoxy)-hexane with a composition containing polymethylvinylsiloxane comprising 99.8 mole % of a dimethylsiloxy unit and 0.2 mole % of a methylvinylsiloxy unit, having both ends each terminated by a dimethylvinylsilyl group and having a polymerization degree of 7,000 and precipitated silica, heating the mixture at 180° C. under pressurization and then further heating it at 200° C.;

A-6: a grease composition having a siloxane content of 85% and containing polydimethylsiloxane having a viscosity at 25° C. of 500 cSt and aerosol silica subjected to surface treatment with hexamethyldisilazane; and A-7: a transparent silicone gel obtained by curing a composition containing polydimethylsiloxane having a viscosity at 25° C. of 700 cSt in which 50% of terminal groups are terminated by dimethylvinylsilyl groups and remaining groups are terminated by trimethylsilyl groups on average, polymethylhydrogen siloxane comprising 60 mole % of a methylhydrogen siloxy unit and 40 mole % of a dimethylsiloxy unit and having both ends each terminated by a trimethylsilyl group in such an amount that 0.8 of Si—H bond is given based on one end vinyl group in said polysiloxane and a catalytic amount of a platinum compound, by heating at 150° C.

As Component (B), alcoholate compounds as shown below were used.

B-1: a methanol solution having a sodium methylate concentration of 28%;

B-2: an ethanol solution having a sodium ethylate concentration of 15%; and

B-3: a methanol solution having a tetramethyl ammonium methylate concentration of 20%.

In the following tables, abbreviations shown below are used.

| Me: a methyl group |
| Et: an ethyl group |
| Ph: a phenyl group |
| R: Me or Et |

EXAMPLES 1 TO 5

Into reactors made of stainless steel and equipped with a stirrer, a thermometer, a rectifying column and a pressure-reducing device, in which moisture was intercepted, starting materials shown in Table 1 were charged. Reactions were carried out by heating the materials under dry nitrogen atmosphere while stirring under reflux of charged alkoxysilane or alcohol at reaction temperatures shown in Table 1. During the reactions, the systems were maintained substantially in an anhydrous state. After the reaction times shown in Table 1, distillations under normal pressure were started, and in some Examples, distillations under reduced pressure were further carried out to recover alcohols and unreacted alkoxysilanes and organoalkoxysilanes produced by the reactions. In some Examples, formation of octamethylcyclotetrasiloxane was also observed. The upper limits of vessel temperature and the lower limits of pressure during the distillations, the amounts of recovered products which were recovered by the distillations and compositional ratios thereof are shown in Table 1. Also, the yields of dimethyldialkoxysilanes are shown in Table 1. In the reactors after recovery, slurry residues containing solids were left.

TABLE 1

| | | Example | | | | |
|---|---|---|---|---|---|---|
| | | 1 | 2 | 3 | 4 | 5 |
| Charged amount (part) | | | | | | |
| A-2 | | 93 | 93 | 6,500 | 93 | 93 |
| B-1 | | 10 | 10 | 650 | | |
| B-2 | | | | | 3.5 | |
| B-3 | | | | | | 13.3 |
| Si(OMe)₄ | | 104 | 265 | 7,800 | | 260 |
| Si(OEt)₄ | | | | | 356 | |
| EtOH | | | | | 10.4 | |
| Reaction | Temperature (°C.) | 95 to 85 | 100 to 90 | 105 | 120 to 114 | 100 to 90 |
| | Time (h) | 6 | 6 | 5 | 7 | 6 |
| Distillation | Upper limit of vessel temperature (°C.) | 290 | 160 | 285 | 160 | 160 |
| | Lower limit of pressure (Torr) | 30 | 35 | Normal pressure | 35 | Normal pressure |
| Recovered amount (part) | | 141 | 281 | 10,030 | 350 | 248 |
| Recovered ratio (%) | | | | | | |
| MeOH | | 1.5 | 2.9 | 8.1 | | 4.0 |
| EtOH | | | | | 5.2 | |
| Si(OMe)₄ | | 9.0 | 49.3 | 6.7 | | 47.1 |
| Si(OEt)₄ | | | | | 58.0 | |
| (EtO)₃SiOSi(OEt)₃ | | 1.1 | 1.2 | | | |
| Me₂Si(OMe)₂ | | 84.8 | 46.5 | 85.1 | | 48.9 |
| Me₂Si(OEt)₂ | | | | | 36.8 | |
| [Me₂SiO]₄ | | 3.6 | | | | |
| Yield of Me₂Si(OR)₂ (%) | | 88 | 96 | 92 | 71 | 83 |

Example 3 is an example in which a stainless steel reactor having a size different from the other Examples and equipped with the same attachments was used. Similarly, dimethyldimethoxysilane could be recovered in high yield. Further, the distillation residue was applied to centrifugation to recover non-volatile liquid polysiloxane and silica contained in A-2.

EXAMPLES 6 TO 10

As shown in Table 2, by using the same starting materials, catalysts and decomposing agent with the same charged amounts as in Examples 1 to 5, respectively, decomposition reactions of high molecular weight polyorganosiloxanes were carried out under the reaction conditions shown in Table 2. After completion of the reactions, the solid phases were recovered by centrifugation, and then the liquid phases were distilled. As a result, chain-structure polydimethylsiloxanes having both ends each terminated by an alkoxy group were obtained as shown in Table 2, which was different from Examples 1 to 5. The residues obtained after distillations were carried out under a pressure of 20 Torr at up to 250° C. were liquid polyorganosiloxanes having average molecular weights shown in Table 2.

TABLE 2

| | Example | | | | |
|---|---|---|---|---|---|
| | 6 | 7 | 8 | 9 | 10 |
| Charged amount (part) | | | | | |
| A-2 | 93 | 93 | 6,500 | 93 | 93 |
| B-1 | 10 | 10 | 650 | | |
| B-2 | | | | 3.5 | |
| B-3 | | | | | 13.3 |
| Si(OMe)₄ | 104 | 265 | 7,800 | | 260 |
| Si(OEt)₄ | | | | 356 | |
| EtOH | | | | 10.4 | |
| Reaction Temperature (°C.) | 95 to 80 | 100 to 95 | 105 | 120 to 115 | 100 to 85 |
| Time (h) | 6 | 6 | 5 | 7 | 6 |
| Distillation ratio/ liquid phase (%) | | | | | |
| ROH | 2.8 | 1.3 | 2.4 | 4.6 | 10.9 |
| Me₃SiOR | 0.5 | 1.0 | 1.0 | | 0.2 |
| Me₂Si(OR)₂ | 24.3 | 25.6 | 22.7 | 21.9 | 30.6 |
| MeSi(OR)₃ | 0.2 | 0.3 | 0.2 | 0.2 | 1.0 |
| Si(OR)₄ | 6.4 | 25.2 | 8.7 | 19.4 | 30.6 |
| RO[Me₂SiO]₂R | 9.4 | 3.3 | 9.1 | 10.4 | 4.6 |
| RO[Me₂SiO]₃R | 10.2 | 14.0 | 12.9 | 2.5 | 10.5 |
| RO[Me₂SiO]₄R | 5.3 | 8.0 | 5.4 | 10.0 | 3.8 |
| RO[Me₂SiO]₅R | 4.4 | 6.6 | 3.8 | 7.0 | 1.5 |
| RO[Me₂SiO]₆R | 5.6 | 2.1 | 5.6 | 2.2 | 0.4 |
| RO[Me₂SiO]₇R | 4.0 | 0.9 | 3.7 | 4.3 | 0.2 |
| RO[Me₂SiO]₈R | 3.8 | 1.1 | 3.6 | 0.8 | 0.1 |
| Total | 77.1 | 89.4 | 79.0 | 83.3 | 94.3 |
| Yield of Me₂Si(OR)₂ (part) | 43.7 | 46.1 | 2,790 | 96.4 | 76.5 |
| Non-volatile liquid polymer | | | | | |
| Yield (part) | 38.3 | 16.9 | 2,470 | 71.5 | 13.0 |
| Average molecular weight | 820 | 690 | 860 | 630 | 690 |

EXAMPLES 11 AND 12

By using the same reactor as used in Example 1, the same experiments were carried out by the same process as in Example 1 except for reducing the amount of tetramethoxysilane (Example 11) or without using tetramethoxysilane (Example 12) under reflux of methanol. Charged amounts, reaction and distillation conditions and results thereof are shown in Table 3. A-2 was used after sufficient drying, all of B-1, tetramethoxysilane and methanol were dehydrated, and the reactor was maintained in a moisture tight state, whereby the water content in the reaction system was 600 ppm or less. Together with dimethyldimethoxysilane, cyclic polyorganosiloxane low molecular weight compounds and straight polydimethylsiloxane low molecular weight compounds having both ends each terminated by a methoxy group were obtained.

TABLE 3

|  |  | Example | |
|---|---|---|---|
|  |  | 11 | 12 |
| Charged amount (part) | | | |
| A-2 |  | 93 | 93 |
| B-1 |  | 60 | 80 |
| Si(OMe)$_4$ |  | 70 |  |
| MeOH |  | 250 | 158 |
| Reaction | Temperature (°C.) | 90 to 96 | 73 to 88 |
|  | Time (h) | 7 | 6 |
| Distillation | Upper limit of vessel temperature (°C.) | 296 | 280 |
|  | Lower limit of pressure (Torr) | 60 | 70 |
| Recovered amount (part) other than MeOH | | 382 | 290 |
| Recovered ratio except for MeOH (%) | | 88 | 69 |
| Me$_2$Si(OMe)$_2$ |  | 86 | 20.3 |
| MeO[Me$_2$SiO]$_2$Me |  | 2 | 7.2 |
| MeO[Me$_2$SiO]$_3$Me |  | 2 | 6.5 |
| MeO[Me$_2$SiO]$_4$Me |  | 0.5 | 4.2 |
| MeO[Me$_2$SiO]$_5$Me |  | 0.5 | 1.8 |
| [Me$_2$SiO]$_3$ |  | 5 | 25.7 |
| [Me$_2$SiO]$_4$ |  | 3 | 23.4 |
| [Me$_2$SiO]$_5$ |  | 1 | 7.2 |
| [Me$_2$SiO]$_6$ |  | 0.5 | 3.6 |
| Yield of Me$_2$Si(OMe)$_2$ (%) |  | 51.8 | 10.4 |

EXAMPLE 13

By using the same charged amounts as in Example 12 and the same process as in Example 6, after completion of decomposition reaction, centrifugation and neutralization of a liquid phase by sending dry carbon dioxide were carried out, and then the liquid phase was distilled to carry out recovery of reaction products. In the distillate were recovered 26.2% by weight of dimethyldimethoxysilane and 23.9% by weight in total of chain-structure polydimethylsiloxane low molecular weight compounds having 2 to 8 silicon atoms in a molecule and having both ends each terminated by a methoxy group, based on the liquid phase obtained. Further, as a distillation residue, 18.5 parts of non-volatile liquid polysiloxane having an average molecular weight of 610 was recovered.

EXAMPLES 14 TO 16

By using Liquid chain-structure polydiorganosiloxane A-1 or A-3, decompositions of said organosiloxane were carried out at formulation ratios shown in Table 4. That is, in Examples 14 and 16, decomposition and recovery were carried out by using tetramethoxysilane in the same manner as in Example 1, and in Example 15, decomposition and recovery were carried out in the same manner as in Example 12 using no alkoxysilane. The results are as shown in Table 4.

TABLE 4

|  | Example | | |
|---|---|---|---|
|  | 14 | 15 | 16 |
| Charged amount (part) | | | |
| A-1 | 74 | 74 |  |
| A-3 |  |  | 100 |
| B-1 | 40 | 40 | 40 |
| Si(OMe)$_4$ | 13 |  | 13 |
| Reaction Temperature (°C.) | 72 | 72 | 70 |
| Time (h) | 6 | 6 | 5 |
| Distillate/liquid phase (%) | | | |
| MeOH | 4.1 | 28.0 | 10.9 |
| Si(OMe)$_4$ | 1.6 |  | 6.5 |
| Me$_2$Si(OMe)$_2$ | 10.2 | 21.2 | 12.9 |
| Me$_3$SiOMe | 0.7 | 4.7 | 4.9 |
| PhSi(OMe)$_3$ |  |  | 2.2 |
| Ph$_2$Si(OMe)$_2$ |  |  | 25.4 |
| MeO[Me$_2$SiO]$_2$Me | 8.4 | 3.1 | 3.1 |
| MeO[Me$_2$SiO]$_3$Me | 7.8 |  |  |
| MeO[Me$_2$SiO][Ph$_2$SiO]Me |  |  | 10.0 |
| MeO[Me$_2$SiO]$_2$[Ph$_2$SiO]Me |  |  | 1.2 |
| [Me$_2$SiO]$_3$ | 30.6 | 18.5 |  |
| [Me$_2$SiO]$_4$ | 28.1 | 16.8 |  |
| [Me$_2$SiO]$_5$ | 8.4 | 5.2 |  |

EXAMPLES 17 TO 20

By using Compositions A-4 to A-6 containing various high molecular weight polyorganosiloxanes and Crosslinked polyorganosiloxane A-7, decompositions of high molecular weight polydiorganosiloxane were carried out according to Example 1.

In Example 17 using A-5, when 10 parts of B-1 and 183 parts of tetramethoxysilane were added to 93 parts of A-5 and the mixture was reacted at a reflux temperature of tetramethoxysilane for 17 hours, slurrying proceeded easily. Then, under normal pressure and reduced pressure, low boiling point substances were removed by evaporation to recover 11.0 parts of methanol, 102.6 parts of dimethyldimethoxysilane, 0.7 part of methyltrimethoxysilane, 72.0 parts of tetramethoxysilane and 1.5 parts of hexamethoxydisiloxane. From the distillation residue, 31.5 parts of silica was recovered by centrifugation.

In the same manner, also in Example 18 using A-4 and Example 19 using A-6, slurries were formed easily, and 71% (Example 18) and 75% (Example 19) of dimethyldimethoxysilanes were recovered based on the theoretical amounts obtained from the high molecular weight polyorganosiloxanes in A-4 and A-6 used. In Example 20 using A-7, gel substances were decomposed easily, and recovered was 76% of dimethyldimethoxysilane was recovered based on the theoretical amount obtained from the high molecular weight polyorganosiloxane in A-7 used.

EXAMPLE 21

To 28 parts of A-2 were added 60 parts of B-1 and 60 parts of methanol, and the mixture was subjected to decomposition reaction under a pressure of from 1 kgf/cm$^2$ to 4 kgf/cm$^2$ at a temperature of 120° C. After reflux was continued for 7 hours, low boiling point substances were removed by evaporation by raising the vessel temperature to 250° C. under 20 Torr. In the distillate, after methanol was removed by evaporation, 11% by weight in total of cyclic dimethylsiloxane low molecular weight compounds and 63% by weight in total of chain dimethylsiloxanes in having both ends each terminated by a methoxy group. As a distillation residue, 30% by weight of liquid polyorganosiloxane was recovered having a weight average molecular weight of 570 based on the high molecular weight polyorganosiloxane of A-2.

EXAMPLE 22

To 93 parts of A-2 were added 10 parts of B-1 and 181 parts of methyltrimethoxysilane, and decomposition reaction was carried out while refluxing at a temperature of 87° to 91° C. for 4 hours. After completion of the reaction, rectification was carried out, the vessel temperature was raised to 162° C., and at a maximum distillation temperature of 85° C., 8.4 parts of methanol and 120 parts of dimethyldimethoxysilane were recovered. By further distillation under reduced pressure, 42.4 parts of unreacted methyltrimethoxysilane and 3.6 parts of a condensed dimer thereof (1,1,3,3-tetramethoxy-1,3-dimethyldisiloxane) were recovered. The yield of dimethyldimethoxysilane based on the theoretical amount obtained from the high molecular weight polyorganosiloxane in A-2 used was 97%.

COMPARATIVE EXAMPLES 1 AND 2

The same reactor as used in Example 1 was used, and to 93 parts of A-2 were added 22.4 parts of potassium hydroxide (Comparative example 1) or sodium hydroxide (Comparative example 2) and 200 parts of methanol. The mixture was reacted under reflux of methanol at 70° C. for 9 hours (Comparative example 1) or 15 hours (Comparative example 2). Then, under distillation conditions, low boiling point substances were distilled under normal pressure at up to 100° C. and further under reduced pressure at up to 210° C. Only a small amount (0.78 part in Comparative example 1 or 0.25 part in Comparative example 2) of dimethyldimethoxysilane was obtained, only a small amount (5.38 parts in Comparative example 1 or 0.87 part in Comparative example 2) of octamethylcyclotetrasiloxane was produced, and a large amount of methanol was recovered.

By Reaction (I) of the present invention, a useful organoalkoxysilane can be obtained from a high molecular weight polyorganosiloxane by using relatively mild reaction conditions. Further, in addition to said organoalkoxysilane, at least one of a polyorganosiloxane low molecular weight compound, a non-volatile liquid polyorganosiloxane and a silica can be obtained. As the above high molecular weight polyorganosiloxane, a crosslinking reaction product thereof and a composition containing a filler can be used. In addition, the present invention provides a process for converting it into an organoalkoxysilane having more organic groups bonded to silicon atoms and having a high utility value by using, as a processing agent, an alkoxysilane which is relatively easily available or has a low utility value.

On the other hand, by Reaction (I'), a polyorganosiloxane low molecular weight compound can be obtained from a high molecular weight polyorganosiloxane. Further, in addition to said polyorganosiloxane low molecular weight compound, an organoalkoxysilane and/or a non-volatile liquid polyorganosiloxane can be obtained.

Therefore, the present invention can be used widely as a process for reusing an industrial waste such as a silicone oil, a silicone gel, a silicone grease, an uncured or cured silicone rubber (including a silicone sealing material and a silicone rubber sponge) or a semi-cured or cured silicone resin, etc.

The organoalkoxysilane and the polysiloxane low molecular weight compound having alkoxy groups at both ends which are synthesized and recovered by the present invention are useful as a modifier of various plastics and rubbers and a synthetic starting material of various kinds of organic silicon compounds. Further, the cyclic polyorganosiloxane also obtained by the present invention can be reused as a starting material of a silicone rubber or a silicone oil. The produced silica, the filler recovered from the high molecular polyorganosiloxane-containing composition, etc. can be used as a filler of a rubber, etc.

We claim:

1. A process for recovering a silicon-containing compound from a high molecular weight polyorganosiloxane, which comprises:
   (I) reacting
      (A) a high molecular weight polyorganosiloxane or a composition containing the same,
      (B) in the presence of at least one alcoholate compound selected from the group consisting of an alkali metal alcoholate and a quaternary ammonium alcoholate, with
      (C) an alkoxysilane, at a temperature of lower than 300° C.; and
   (II) recovering the resulting
      (a) an organoalkoxysilane; or at least one of the following (b) to (d) in addition to said (a)
      (b) a distillable polyorganosiloxane low molecular weight compound;
      (c) a non-volatile liquid polyorganosiloxane having a weight average molecular weight of less than 1,000; and
      (d) a silica.

2. The process according to claim 1, wherein (A) is a chain-structure polyorganosiloxane or a composition containing the same.

3. The process according to claim 2, wherein (A) is a cured composition.

4. The process according to claim 3, wherein (C) is used in such an amount that the total number of alkoxy groups existing in (B) and (C) is 1 or more based on one silicon atom existing in the high molecular weight polyorganosiloxane in (A).

5. The process according to claim 2, wherein substantially all organic groups bonded to silicon atoms of the chain-structure polyorganosiloxane are methyl groups.

6. The process according to claim 1, wherein (A) is an industrial waste.

7. The process according to claim 1, wherein Reaction (I) is carried out in the presence of
   (D) an alcohol represented by the formula: $R^3OH$, wherein $R^3$ represents an alkyl group with a carbon number of 1 to 6.

8. The process according to claim 2, wherein Reaction (I) is carried out in a slurry state.

9. The process according to claim 7, wherein (B) is an alkali metal methylate, and (D) is methanol.

10. The process according to claim 1, wherein Reaction (I) is carried out under a condition that the water content in the reaction system is 3,000 ppm or less.

11. The process according to claim 1, wherein component (C), the alkoxysilane, is represented by the formula:
$R^1{}_m Si(OR^2)_{4-m}$, wherein $R^1$ represents a substituted or unsubstituted monovalent hydrocarbon group with a carbon number of 1 to 6; $R^2$ represents an alkyl group with a carbon number of 1 to 6; and m is 0, 1 or 2 and/or a partially hydrolyzed condensate thereof in such an amount that the total number of alkoxy groups existing in the above (B) and (C) is 0.1 or more based on one silicon atom existing in the high molecular weight polyorganosiloxane in (A), or in such an amount that the above total number of alkoxy groups is 0.1 or more and less than 1 when (A) is a liquid or semi-solid chain-structure polydiorganosiloxane; compound (a), the organoalkoxysilane, is represented by the formula: $R^4{}_n Si(OR^5)_{4-n}$, wherein $R^4$ represents a substituted or unsubstituted monovalent hydrocarbon group derived from $R^1$ and the polyorganosiloxane; $R^5$ represents an alkyl group with a carbon number of 1 to 6; and n is 1, 2 or 3 and also an integer satisfying n>m; and the distillable polyorganosiloxane low molecular weight compound has 2–8 silicon atoms in the molecule.

12. The process according to claim 11, wherein $R^1$ is selected from the group consisting of a straight or branched methyl, ethyl, propyl, butyl, pentyl and hexyl group, a cycloalkyl group, a phenyl group, and a chloromethyl group; and $R^4$ is selected from the group consisting of 3,3,3-trifluoropropyl, 3-aminopropyl, N-(2-aminoethyl)-3-aminopropyl, and 3-glycidoxypropyl.

13. The process according to claim 11, wherein (C) is an alkoxysilane in which m=0.

14. The process according to claim 11, wherein $R^2$ of (C) is methyl, Reaction (I) is carried out in a slurry, and (A) is a chain-structure polyorganosiloxane or a composition containing the same.

15. The process according to claim 1, wherein (b) is a cyclic polydiorganosiloxane low molecular weight compound.

16. The process according to claim 1, wherein (b) is a polydiorganosiloxane low molecular weight compound having both ends each terminated by an alkoxy group.

17. The process according to claim 7, wherein distillation is carried out at the boiling point of (a), or a temperature which is not lower than the azeotropic temperature of (a) and (D) and is lower than the boiling point of (C).

18. The process according to claim 1, wherein (b) is removed by evaporation after deactivating or removing (B) existing in the production system of Reaction (I).

19. The process according to claim 1, further comprising recovering a filler and/or a pigment from (A).

20. A process for recovering a silicon-containing compound from a high molecular weight polyorganosiloxane, which comprises:

(I') reacting
 (A) a high molecular weight polyorganosiloxane or a composition containing the same with
 (B) at least one alcoholate compound selected from the group consisting of an alkali metal alcoholate and a quaternary ammonium alcoholate, under conditions of a reaction temperature of 50° to 150° C. and a water content in the reaction system of 3,000 ppm or less; and (II') recovering the resulting
 (b) a distillable polyorganosiloxane low molecular weight compound; or at least one of the following (a) and (c) in addition to said (b)
 (a) an organoalkoxysilane; and
 (c) a non-volatile liquid polyorganosiloxane having a weight average molecular weight of less than 1,000.

21. The process according to claim 20, wherein (A) is a chain-structure polyorganosiloxane or a composition containing the same.

22. The process according to claim 21, wherein (A) is a cured composition.

23. The process according to claim 21, wherein substantially all organic groups bonded to silicon atoms of the chain-structure polyorganosiloxane are methyl groups.

24. The process according to claim 20, wherein (A) is an industrial waste.

25. The process according to claim 20, wherein Reaction (I') is carried out in the presence of
 (D) an alcohol represented by the formula: $R^3OH$.

26. The process according to claim 21, wherein Reaction (I') is carried out in a slurry state.

27. The process according to claim 25, wherein (B) is an alkali metal methylate, and (D) is methanol.

28. The process according to claim 20, wherein (b) is a cyclic polysiloxane low molecular weight compound.

29. The process according to claim 20, wherein (b) is a polydiorganosiloxane low molecular weight compound having both ends each terminated by an alkoxy group.

30. The process according to claim 20, wherein (b) is removed by evaporation after deactivating or removing (B) existing in the production system of Reaction (I').

31. The process according to claim 20, further comprising recovering a filler and/or a pigment from (A).

32. The process according to claim 20, wherein compound (a), the organoalkoxysilane, is represented by the formula:

$R^4{}_n Si(OR^5)_{4-n}$, wherein $R^4$ represents a substituted or unsubstituted monovalent hydrocarbon group derived from $R^1$ and the polyorganosiloxane; $R^5$ represents an alkyl group with a carbon number of 1 to 6; and n is 1, 2 or 3 and also an integer satisfying n>m; $R^1{}_m Si(OR^2)_{4-m}$, $R^1$ represents a substituted or unsubstituted monovalent hydrocarbon group with a carbon number of 1 to 6; and the distillable polyorganosiloxane low molecular weight compound has 2–8 silicon atoms in the molecule.

33. The process according to claim 32, wherein $R^1$ is selected from the group consisting of a straight or branched methyl, ethyl, propyl, butyl, pentyl and hexyl group, a cycloalkyl group, a phenyl group, and a chloromethyl group; and $R^4$ is selected from the group consisting of 3,3,3-trifluoropropyl, 3-aminopropyl, N-(2-aminoethyl)-3-aminopropyl, and 3-glycidoxypropyl.

* * * * *